US012620453B2

(12) United States Patent
Choi et al.

(10) Patent No.: US 12,620,453 B2
(45) Date of Patent: May 5, 2026

(54) METHOD, APPARATUS, AND COMPUTER PROGRAM FOR PREDICTING INTERACTION OF COMPOUND AND PROTEIN

(71) Applicant: ONCOCROSS CO., LTD., Seoul (KR)

(72) Inventors: Jin Woo Choi, Gyeonggi-do (KR); Yi Rang Kim, Sejong (KR)

(73) Assignee: ONCOCROSS CO., LTD., Seoul (KR)

( * ) Notice: Subject to any disclaimer, the term of this patent is extended or adjusted under 35 U.S.C. 154(b) by 983 days.

(21) Appl. No.: 17/789,333

(22) PCT Filed: Dec. 14, 2020

(86) PCT No.: PCT/KR2020/018235
§ 371 (c)(1),
(2) Date: Jun. 27, 2022

(87) PCT Pub. No.: WO2021/137470
PCT Pub. Date: Jul. 8, 2021

(65) Prior Publication Data
US 2023/0063188 A1 Mar. 2, 2023

(30) Foreign Application Priority Data

Jan. 2, 2020 (KR) ........................ 10-2020-0000318
Dec. 7, 2020 (KR) ........................ 10-2020-0169587

(51) Int. Cl.
*G16B 15/00* (2019.01)
*G06N 3/04* (2023.01)
(Continued)

(52) U.S. Cl.
CPC ............ *G16B 15/00* (2019.02); *G06N 3/044* (2023.01); *G06N 3/045* (2023.01); *G16B 30/00* (2019.02); *G16B 40/20* (2019.02)

(58) Field of Classification Search
CPC ............................... G06N 3/045; G06N 3/044
See application file for complete search history.

(56) References Cited

FOREIGN PATENT DOCUMENTS

KR 10-2019-0049537 A 5/2019

OTHER PUBLICATIONS

Lee I, Keum J, Nam H (2019) DeepConv- DTI: Prediction of drug-target interactions via deep learning with convolution on protein sequences. PLoS Comput Biol 15(6): e1007129. https://doi.org/10.1371/journal.pcbi.1007129 (Year: 2018).*

(Continued)

*Primary Examiner* — David Yi
*Assistant Examiner* — Paul Coleman
(74) *Attorney, Agent, or Firm* — Harness, Dickey & Pierce, P.L.C.

(57) ABSTRACT

Provided are a method, an apparatus, and a computer program for predicting interaction between a compound and a protein. A method for predicting interaction between a compound and a protein according to some embodiments of the present disclosure may comprises the steps of: acquiring learning data composed of compound data for learning, protein data for learning, and interaction scores; constructing a deep-learning model by using the acquired learning data; and predicting interaction of a given compound and protein through the constructed deep-learning model. Through the learning of the deep-learning mode with the exclusion of amino acid sequences associated with protein domains having a negative influence on interactions from amino acid sequences of proteins for learning, the interaction between a given compound and protein in the in vivo environment can be accurately predicted.

12 Claims, 14 Drawing Sheets

(51) Int. Cl.

| | |
|---|---|
| *G06N 3/044* | (2023.01) |
| *G06N 3/045* | (2023.01) |
| *G16B 30/00* | (2019.01) |
| *G16B 40/20* | (2019.01) |

(56) References Cited

OTHER PUBLICATIONS

Mohammed AlQuraishi, ProteinNet: a standardized data set for machine learning of protein structure, https://doi.org/10.1186/s12859-019-2932-0 (Year: 2019).*

Basic Neurochemistry: Molecular, Cellular and Medical Aspects. 6th edition, Membrane Proteins, R Wayne Albers. (Year: 1999).*

An introduction to deep learning on biological sequence data: examples and solutions. Bioinformatics. 2017 (Year: 2017).*

Cooper GM. The Cell: A Molecular Approach. 2nd edition. Sunderland (MA): Sinauer Associates; 2000. Functions of Cell Surface Receptors. Available from: https://www.ncbi.nlm.nih.gov/books/NBK9866/ (Year: 2000).*

International Search Report from corresponding PCT Application No. PCT/KR2020/018235, dated May 7, 2021.

Seo, S., et al.; "Prediction of Compound-Protein Interactions Using Deep Learning", Journal of KIISE, Oct. 2019, vol. 46, No. 10, pp. 1054-1060.

Ozturk, H., et al.; "WideDTA: prediction of drug-targeted binding affinity", Feb. 2019, pp. 1-11.

Tsubake, M., et al.; "Compound-protein interaction prediction with end-to-end learning of neural networks for graphs and sequences", Bioinformatics, Jan. 15, 2019, vol. 35, No. 2, pp. 309-318.

Zheng, S., et al.; "Predicting drug protein interaction using quasi-visual question answering system". bioRxiv, Mar. 25, 2019, pp. 1-7.

Office Action from corresponding U.S. Appl. No. 18/036,312, dated Aug. 8, 2025.

Jurtz VI, Johansen AR, Nielsen M, Almagro Armenteros JJ, Nielsen H, Sa/\derby CK, Winther 0, Sa/\nderby SK. An introduction to deep learning on biological sequence data: examples and solutions. Bioinformatics. Nov. 1, 20175.

Cooper GM. The Cell: A Molecular Approach. 2nd edition. Sunderland (MA): Sinauer Associates; 2000. Functions of Cell Surface Receptors. Available from: https://www.ncbi.nlm.nih.gov/books/NBK9866.

Lee I, Keum J, Nam H (2019) DeepConv- DTI: Prediction of drug-target interactions via deep learning with convolution on protein sequences. PLoS Comput Biol 15(6): e1007129. https://doi.org/10.1371/joumal.pcbi.1007129; 2019.

Mohammed AlQuraishi, ProteinNet: a standardized data set for machine learning of protein structure, https://doi.org/10.1186/ S12859-019-2932-0; 2019.

Basic Neurochemistry: Molecular, Cellular and Medical Aspects. 6th edition, Membrane Proteins, R Wayne Albers.

WideDTA: prediction of drug-target binding affinity; H Ozturk, E Ozkirimli, A Ozgur; arXiv preprint arXiv: 1902.04166, 2019'arxiv.org.

* cited by examiner

FIG. 2

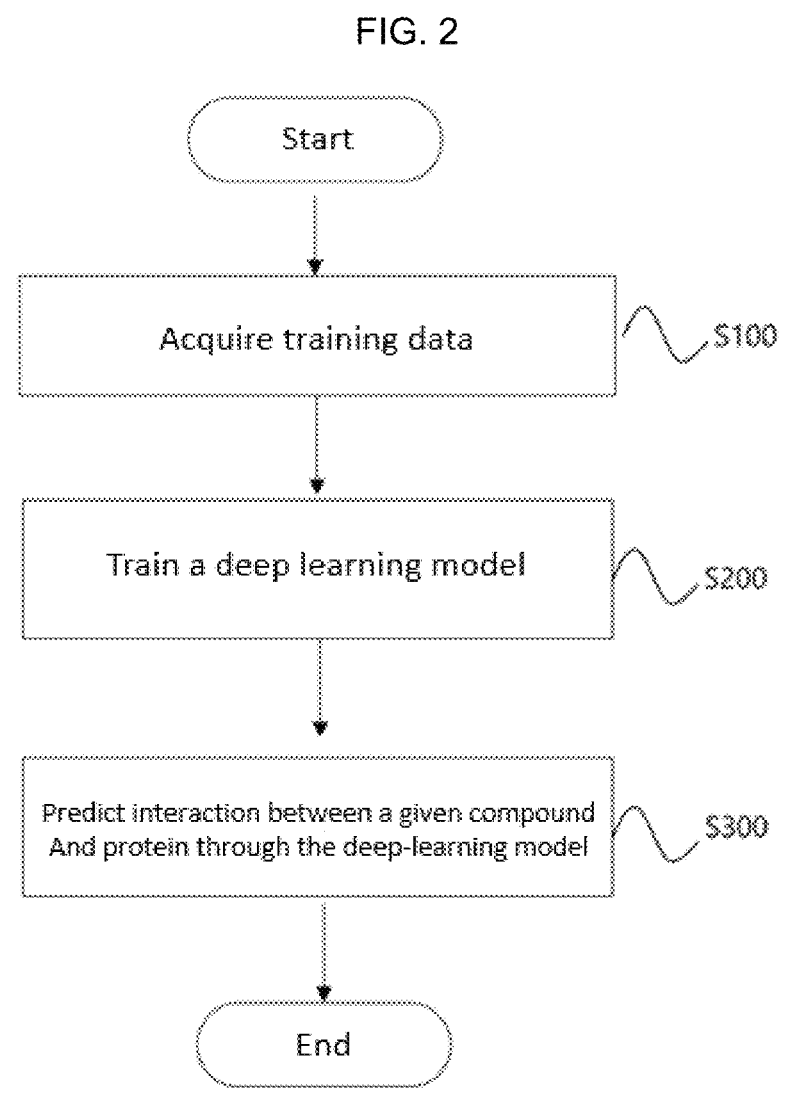

```
            ┌──────────┐
            │  Start   │
            └──────────┘
                 ┆
                 ▼
    ┌──────────────────────────────┐
    │     Acquire training data    │ ⎯⎯ S100
    └──────────────────────────────┘
                 ┆
                 ▼
    ┌──────────────────────────────┐
    │   Train a deep learning model│ ⎯⎯ S200
    └──────────────────────────────┘
                 ┆
                 ▼
    ┌──────────────────────────────────────┐
    │ Predict interaction between a given   │ ⎯⎯ S300
    │ compound And protein through the      │
    │ deep-learning model                   │
    └──────────────────────────────────────┘
                 ┆
                 ▼
            ┌──────────┐
            │   End    │
            └──────────┘
```

METHOD, APPARATUS, AND COMPUTER PROGRAM FOR PREDICTING INTERACTION OF COMPOUND AND PROTEIN

CROSS-REFERENCE TO RELATED APPLICATIONS

This application is a national phase application of PCT Application No. PCT/KR2020/018235, filed on Dec. 14, 2020, which claims priority to Korean Patent Application Nos. 10-2020-0000318, filed on Jan. 2, 2020 and 10-2020-0169587, filed on Dec. 7, 2020. The entire disclosure of the applications identified in this paragraph is incorporated herein by reference.

TECHNICAL FIELD

The present disclosure relates to a method, an apparatus, and a computer program for predicting disease. More specifically, the present disclosure relates to a method for predicting the presence or extent of interaction between a given compound and protein using a deep-learning model, an apparatus for performing the method, and a computer program in which the method is implemented.

BACKGROUND ART

By using computational methods and bio-informatics, researchers may find new uses of existing compounds or predict the uses of new compounds. This approach is widely used in the discovery of new drugs.

The discovery and development of new drugs always takes a lot of time and money and goes through a complex process. Accordingly, in recent years, research has been actively carried out to combine disciplines from various fields such as bio-informatics, chemi-informatics, computer science, and computer-aided drug discovery/design (CADD) to reduce the time required for the discovery and development of new drugs and to enhance the effects of new drugs.

However, since the prior art employs a rule-based approach, it is impossible to predict a situation in which a rule may not be defined beyond human recognition.

SUMMARY

The technical object to be achieved through some embodiments of the present disclosure is to provide a method for accurately predicting the presence or extent of interaction between a given compound and protein using a deep-learning model, an apparatus for performing the method, and a computer program in which the method is implemented.

Another technical object to be achieved through some embodiments of the present disclosure is to provide a method for accurately predicting the presence or extent of interaction between a compound and a protein in the in vivo environment using a deep-learning model, an apparatus for performing the method, and a computer program in which the method is implemented.

Technical objects of the present disclosure are not limited to those described above, and other technical objects not mentioned above may also be clearly understood from the descriptions given below by those skilled in the art to which the present disclosure belongs.

To achieve the technical object above, a method for predicting interaction between a compound and a protein according to some embodiments of the present disclosure comprises, as a method for predicting interaction between a compound and a protein in a computing device, acquiring training data composed of compound data for learning, protein data for learning, and interaction scores; constructing a deep-learning model by using the acquired training data; predicting interaction between a given compound and protein through the constructed deep-learning model, wherein the protein data for learning may include amino acid sequences of the protein for learning, and the constructing may include generating first training data by excluding amino acid sequences associated with a first protein domain having a negative influence on the interaction from the amino acid sequences of the protein for learning; and training the deep-learning model based on the first training data.

In some embodiments, the first protein domain may include a transmembrane domain.

In some embodiments, the constructing includes generating second training data consisting of the compound data for learning, amino acid sequence data associated with the first protein domain, and a first interaction score; and training the deep-learning model using the second training data, wherein the first interaction score may be determined based on the extent to which the first protein domain negatively affects the interaction.

In some embodiments, the constructing includes: selecting a first plurality of proteins for learning whose interaction score with a specific compound for learning is above a threshold and a second plurality of proteins for learning whose interaction score is below the threshold from the acquired training data; comparing amino acid sequences of the first plurality of proteins for learning and extracting a first common sequence; comparing amino acid sequences of the second plurality of proteins for learning and extracting a second common sequence; training the deep-learning model using second training data consisting of the first common sequence, the specific compound data for learning, and a first interaction score; and training the deep-learning model using third learning data consisting of the second common sequence, the specific compound data for learning, and a second interaction score, wherein the first interaction score may be set to a value higher than an average interaction score of the first plurality of proteins for learning, and the second interaction score may be set to a value lower than the average interaction score of the first plurality of proteins for learning.

In some embodiments, the constructing includes: analyzing the acquired training data to select first protein data for learning whose interaction score with a specific compound for learning is equal to or greater than a threshold and a second protein for learning whose interaction score is equal to or lower than the threshold; comparing an amino acid sequence of the first protein for learning with an amino acid sequence of the second protein for learning to extract a non-common sequence; acquiring a predicted interaction score for the non-common sequence and the specific compound for learning through the deep-learning model; determining an interaction score for learning based on the predicted interaction score; and training the deep-learning model using second training data consisting of the non-common sequence, the specific compound data for learning, and the determined interaction score.

To achieve the technical object above, an apparatus for predicting interaction between a compound and a protein according to some embodiments of the present disclosure may comprise a memory storing one or more instructions and a processor performing an operation of acquiring training data consisting of compound data for learning, protein data for learning, and interaction scores, an operation of constructing a deep-learning model using the acquired training data, and an operation of predicting interaction between a given compound and protein through a deep-learning model through the constructed deep-learning model by executing the one or more stored instructions. At this time, the protein data for learning may include amino acid sequences of the protein for learning, and the constructing operation may include an operation of generating first training data by excluding amino acid sequences associated with a first protein domain having a negative influence on the interaction from the amino acid sequences of the protein for learning and an operation of training the deep-learning model based on the first training data.

To achieve the technical object above, a computer program according to some embodiments of the present disclosure may be stored in a computer-readable recording medium for executing: acquiring training data consisting compound data for learning, protein data for learning, and interaction scores in conjunction with a computing device; constructing a deep-learning model using the acquired training data; and predicting interaction between a given compound and protein through the constructed deep-learning model. At this time, the protein data for learning may include amino acid sequences of the protein for learning, and the constructing may include generating first training data by excluding amino acid sequences associated with a first protein domain having a negative influence on the interaction from the amino acid sequences of the protein for learning and training the deep-learning model based on the first training data.

Advantageous Effects

According to some embodiments of the present disclosure, interaction between a given compound and protein may be accurately predicted through a deep-learning model.

Also, a deep-learning model may be trained by excluding amino acid sequences associated with protein domains negatively affecting interaction in vivo from amino acid sequences of proteins for learning, or the deep-learning model may be trained separately using associated sequences. As a result, the deep-learning model may accurately predict interaction between a given compound and protein in an actual in vivo environment, thereby greatly improving the utility of the deep-learning model.

The advantageous effects due to the technical principles of the present disclosure are not limited to those described above, and other effects not mentioned above may be clearly understood from the descriptions given below by those skilled in the art to which the present disclosure belongs.

BRIEF DESCRIPTION OF THE DRAWINGS

FIG. 2 is a flow diagram illustrating a method for predicting interaction between a compound and a protein according to some embodiments of the present disclosure.

FIGS. 5 and 6 illustrate a structure of a deep-learning model and a method for training the deep-learning model according to a second embodiment of the present disclosure.

FIG. 14 illustrates a deep-learning model according to some embodiments of the present disclosure.

DESCRIPTION OF EXEMPLARY EMBODIMENTS

In what follows, preferred embodiments of the present disclosure will be described in detail with reference to appended drawings. The advantages and features of the present disclosure, and a method for achieving them will be clearly understood with reference to the embodiments described in detail together with appended drawings. However, the technical principles and spirit of the present disclosure are not limited to the embodiments disclosed below but may be implemented in various other forms; rather, the present embodiments are provided to make the present disclosure complete and inform those skilled in the art clearly of the technical scope of the present disclosure, and the technical principles and spirit of the present disclosure may be defined within the technical scope of the appended claims.

In assigning reference symbols to the constituting elements of each drawing, it should be noted that the same constituting elements are intended to have the same symbol as much as possible, even if they are shown on different drawings. Also, in describing the present disclosure, if it is determined that a detailed description of a related well-known configuration or function incorporated herein unnecessarily obscure the gist of the present disclosure, the detailed description thereof will be omitted.

Unless otherwise defined, all terms (including technical and scientific terms) used herein may be used in a sense commonly understood by those skilled in the art to which the present disclosure belongs. Also, terms defined in commonly used dictionaries are not ideally or excessively interpreted unless otherwise explicitly defined. The terms used herein are intended to describe embodiments and are not intended to limit the present disclosure. In the present disclosure, a singular expression includes a plural expression unless clearly indicated otherwise in the corresponding phrase.

Also, in describing the constituting elements of the present disclosure, terms such as first, second, A, B, (a), and (b) may be used. Such terms are intended only to distinguish one constituting element from the others and do not limit the nature, sequence, or order of the constituting elements. If a constituting element is said to be "linked to," "combined with," or "connected to" a different constituting element, it should be understood that the constituting element is linked or connected to the different constituting element, but another constituting element may be "linked," "combined," or "connected" between the two constituting elements.

The term "comprises" and/or "comprising" used in the present disclosure indicates the existence of a constituting element, a step, an operation, and/or a component described but does not exclude the existence or addition of one or more other constituting elements, steps, operations, and/or components.

In what follows, various embodiments of the present disclosure will be described in detail with reference to appended drawings.

Figure 1:
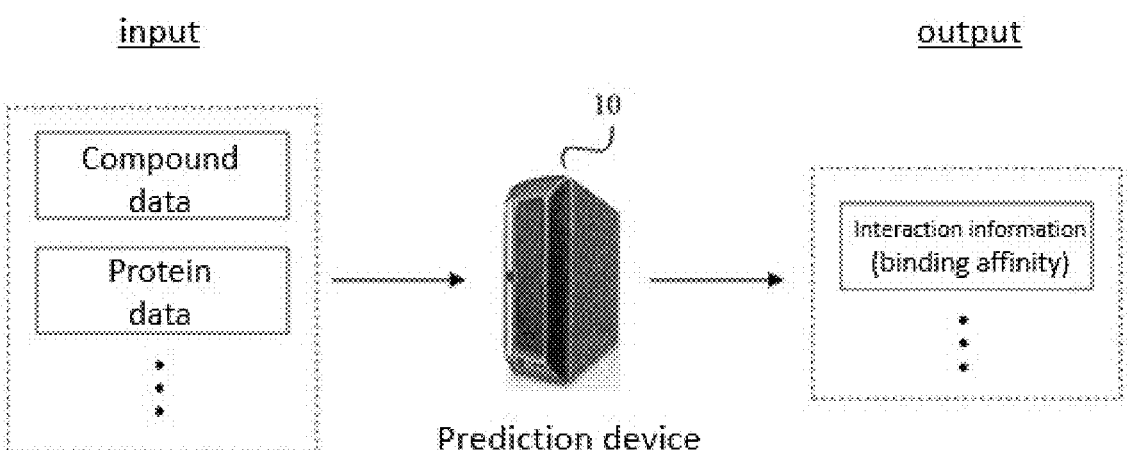
FIG. 1 illustrates an apparatus for predicting interaction between a compound and a protein according to some embodiments of the present disclosure and input and output data of the apparatus.

FIG. 1 illustrates an apparatus 10 for predicting interaction between a compound and a protein according to some embodiments of the present disclosure and input and output data of the apparatus.

As shown in FIG. 1, the apparatus 10 for predicting interaction may be a computing device that predicts and outputs interaction information (e.g., binding affinity) of input compound and protein based on input data such as compound data and protein data. For example, if the input compound is a drug and the input protein is a target protein predicted to induce disease, the apparatus 10 for predicting interaction may predict drug-target interactions (DTI) information. In this case, the apparatus 10 for predicting interaction may be effectively utilized to derive new candidate substances in a drug development process. In what follows, for the convenience of descriptions, the apparatus 10 for predicting interaction is abbreviated to a "prediction device 10."

Figure 15:
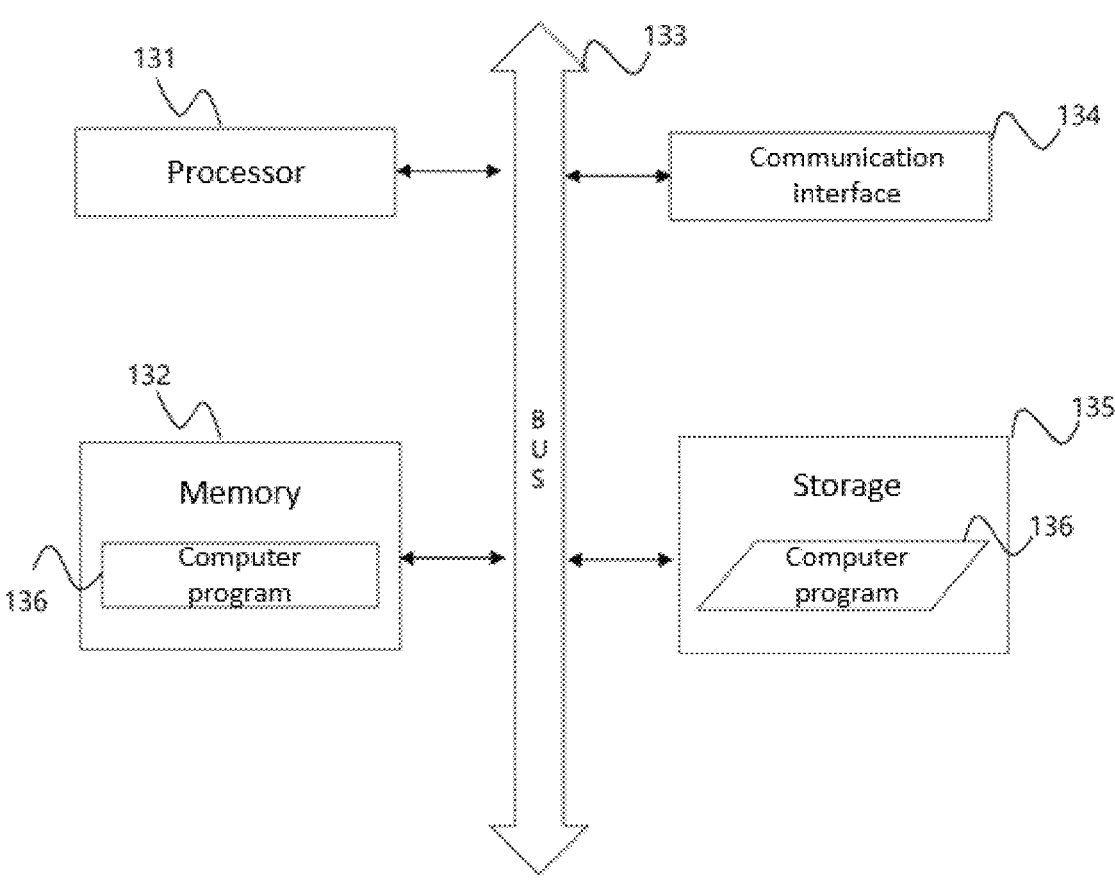
FIG. 15 illustrates a computing device capable of implementing an apparatus for predicting interaction between a compound and a protein according to some embodiments of the present disclosure.

The computing device may be, but is not limited to, a notebook, a desktop, or a laptop computer, which may include all kinds of devices equipped with computing capabilities. FIG. 15 shows one example of a computing device.

More specifically, the prediction device 10 may predict interaction between a compound and a protein using a deep-learning model. At this time, the deep-learning model may be implemented based on various kinds of neural network models and may be designed in various structures. The neural network model may include, for example, an artificial neural network (ANN), a convolutional neural network (CNN), a recurrent neural network (RNN), or a combination thereof but is not limited thereto. A detailed structure and a learning method of the deep-learning model will be described with reference to the drawings of FIG. 2 and subsequent figures.

The compound data may include, for example, data on the compound formula, functional group, molar mass, members, binding structure, electron number, and acidity of the compound but may further include various data without being limited thereto or may not include any of the data above.

The protein data may include, for example, an amino acid sequence of the protein, amino acid residues, tissue-specific or patient-specific expression patterns of the protein, and the protein's role in a specific cell signal transduction system but may further include various data without being limited thereto or may not include any of the data above.

The interaction information may include scores on various indicators related to the interaction, such as binding affinity, cohesion, and binding force. However, the interaction information is not limited thereto. In what follows, for the convenience of understanding, descriptions are continued based on the assumption that the interaction information is a score ("interaction score") indicating the degree of interaction.

In some embodiments, the prediction device 10 may further predict the use (or efficacy) of a compound. Specifically, the prediction device 10 may output a list of proteins that are expected to interact with a given compound using a deep-learning model. For example, the prediction device 10 may predict the interaction score between a given compound and various proteins by inputting data of the given compound and data of a specific protein into the deep-learning model while changing the specific protein type. The prediction device 10 may then output a list of proteins consisting of proteins whose predicted interaction score is above a threshold. In addition, the prediction device 10 may predict the use or efficacy of the compound based on the common characteristics of the proteins included in the protein list. For example, if proteins included in the protein list exhibit different aspects of expression pattern in a patient sample of a particular disease, the prediction device 10 may predict that the given compound has efficacy for that disease. Also, if the proteins included in the protein list are associated with a specific side effect, the prediction device 10 may predict that the given compound is highly likely to be associated with the side effect.

Meanwhile, although FIG. 1 shows an example in which the prediction device 10 is implemented by one computing device, the prediction device 10 may be implemented by a plurality of computing devices. In this case, a first function of the prediction device 10 may be implemented in a first computing device, and a second function may be implemented in a second computing device. Alternatively, a specific function of the prediction device 10 may be implemented in a plurality of computing devices.

Up to now, the prediction device 10 according to some embodiments of the present disclosure and its input and output data have been briefly described with reference to FIG. 1. In what follows, a method for predicting interaction of a compound and a protein will be described with reference to the drawings of FIG. 2 and subsequent figures.

A computing device may perform each step of a method for predicting interaction to be described below. In other words, each step of the method may be implemented using one or more instructions executed by a processor of the computing device. All the steps included in the method may be executed by one physical computing device but may be executed by being distributed over a plurality of physical computing devices. For example, a first computing device may perform first steps of the method, and a second computing device may perform second steps of the method. In what follows, descriptions will be given based on the assumption that each step of the method is performed by the prediction device 10 illustrated in FIG. 1. Therefore, if a subject is omitted for each operation in the following description, it may be understood that the operation is performed by the illustrated apparatus 10. However, in some cases, some steps of the method may be performed on another computing device.

FIG. 2 is a flow diagram illustrating a method for predicting interaction between a compound and a protein according to some embodiments of the present disclosure. However, the flow diagram is only a preferred embodiment for achieving the object of the present disclosure, and it should be understood that some steps may be added or deleted depending on the needs.

As shown in FIG. 2, the method for predicting interaction may start at step S100 of acquiring the training data (set).

Here, the training data (or samples constituting the training data) may be composed of compound data for learning, protein data for learning, and interaction information (i.e., ground truth interaction information), wherein the interaction information may be, for example, an interaction score that expresses the presence or extent of the interaction numerically.

The training data may be acquired from a public DB such as DrugBank or Pubchem, which is not limited thereto.

In step S200, the deep-learning model may be trained using the acquired training data. For example, the prediction device 10 may train a deep-learning model by acquiring a predicted interaction score by entering each sample constituting the training data into the deep-learning model, calculating a prediction error based on the difference between the predicted interaction score and the ground truth interaction score, and backpropagating the calculated prediction error. Here, training may mean that weights of the deep-learning model are updated to minimize prediction errors.

Figure 3:
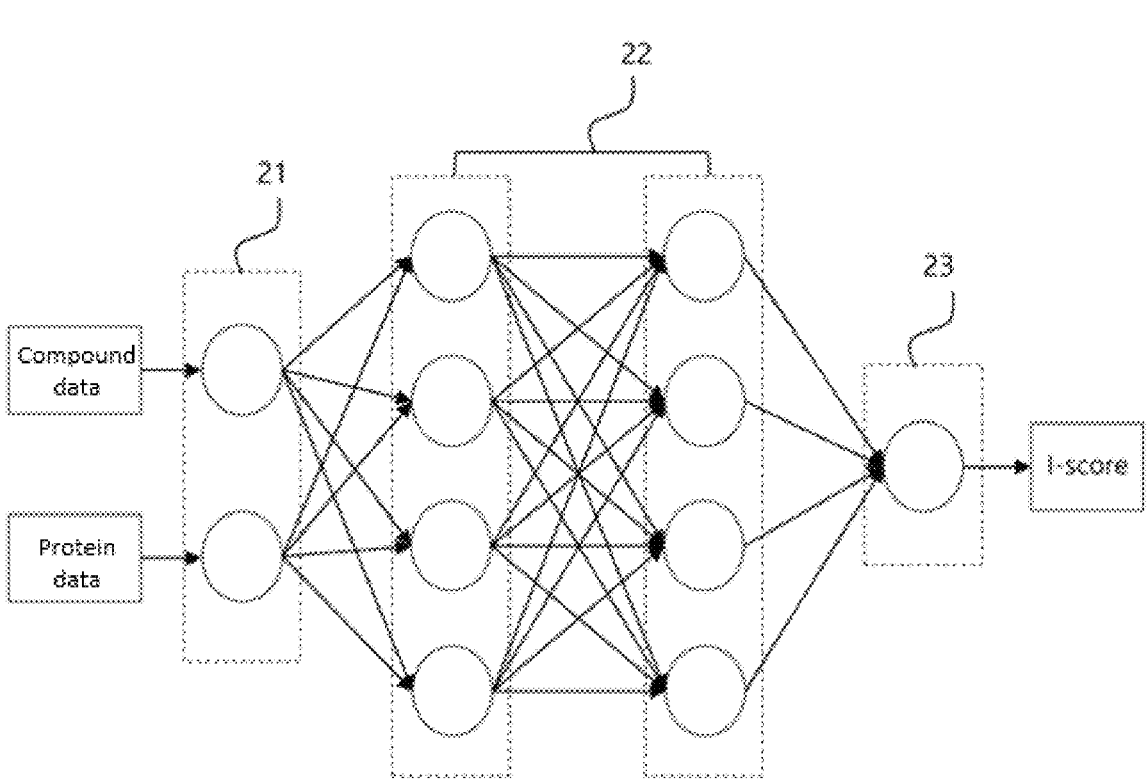
FIG. 3 illustrates an artificial neural network-based deep-learning model according to some embodiments of the present disclosure.

As described above, deep-learning models may be implemented (constructed) based on various types of neural network models. For example, as illustrated in FIG. 3, a deep-learning model may be implemented based on ANN. At this time, ANN may be composed of an input layer 21, a hidden layer 22, and an output layer 23, wherein the input layer 21 is designed to receive compound data and protein data, and the output layer 23 may be designed to output interaction scores (I-scores) but are not limited thereto. Since those skilled in the art should be fully informed of the functions, operating principles, and basic training methods of each layer that makes up the ANN, detailed descriptions thereof will be omitted.

It should be noted that compound data may be converted into fingerprint data by a compound fingerprint technique such as circular fingerprinting and input to a deep-learning model. However, the technical scope of the present disclosure is not limited thereto.

A detailed structure of a deep-learning model and a specific method for training the deep-learning model according to an embodiment will be described with reference to the drawings of FIG. 4 and subsequent figures.

Again, descriptions will be given with reference to FIG. 2.

In step S300, the interaction between a given compound and protein may be predicted through a deep-learning model constructed. For example, the prediction device 10 may input data of the given compound and data of the protein into the deep-learning model to predict an interaction score.

Up to now, a method for predicting interaction between a compound and a protein according to some embodiments of the present disclosure has been described with reference to FIG. 2. In what follows, various embodiments of the present disclosure related to the structure of a deep-learning model and a method for training the deep-learning model will be described.

Figure 4:
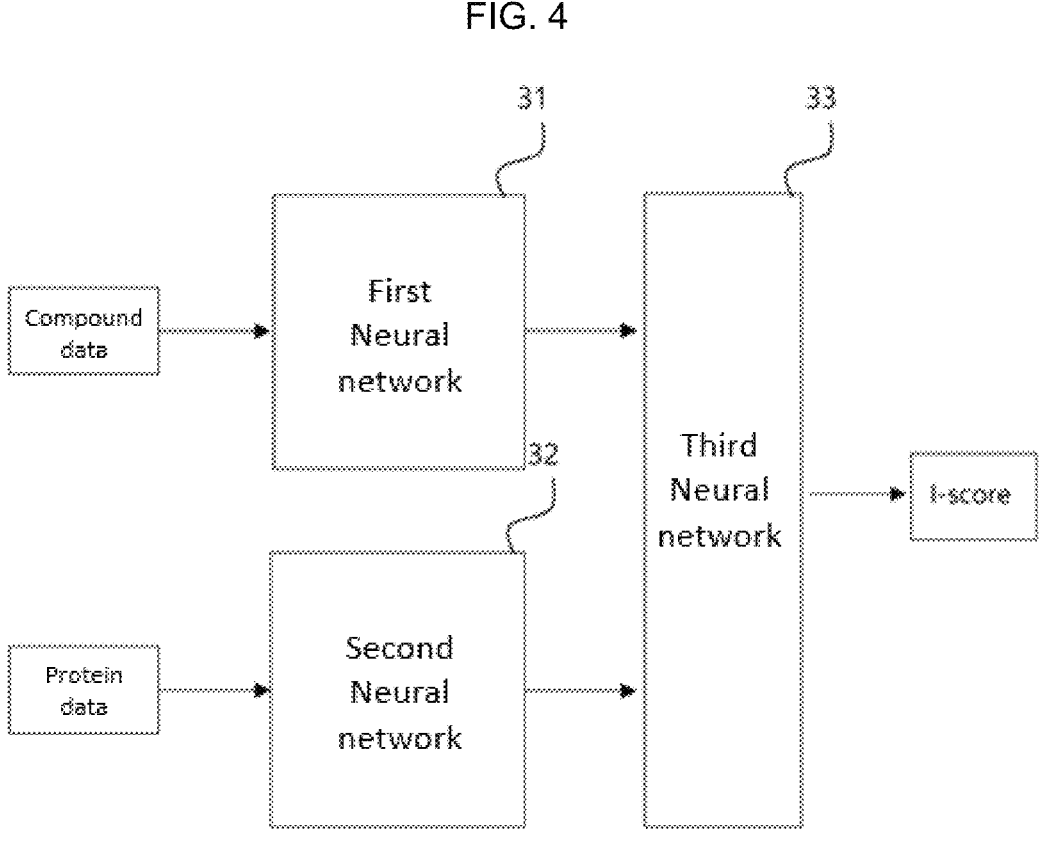
FIG. 4 illustrates a structure of a deep-learning model and a method for training the deep-learning model according to a first embodiment of the present disclosure.

FIG. 4 illustrates a structure of a deep-learning model and a method for training the deep-learning model according to a first embodiment of the present disclosure.

As shown in FIG. 4, a deep-learning model in the present embodiment may comprise a first neural network 31 receiving compound data, a second neural network 32 receiving protein data, and a third neural network 33 outputting an interaction score.

The first neural network 41 may be trained to extract feature data of an input compound by performing neural network operations on the input compound data. The first neural network 31 may be trained to accurately extract feature data unique to the compound by being composed of the second neural network 32 and an independent network. As mentioned earlier, the compound data may be converted into fingerprint data and input to the first neural network 31, but the scope of the present disclosure is not limited thereto. The first neural network 41 may be implemented based on various types of neural networks, such as ANN, CNN, and RNN.

Next, the second neural network 32 may be trained to extract feature data of an input protein by performing neural network operations on the input protein data. The second neural network 32 may be constructed independently of the first neural network 31 so that it may be trained to accurately extract feature data unique to proteins. The protein data may include, for example, an amino acid sequence of the protein but are not limited thereto. The second neural network 32 may also be implemented based on various types of neural networks such as ANN, CNN, and RNN.

Next, the third neural network 33 may be trained to analyze the feature data of the compound and protein comprehensively through neural network operations to predict interaction scores. The third neural network 33 may be implemented as a fully connected layer but is not limited thereto.

The first to third neural networks 31-33 may be trained by backpropagating errors based on the difference of a predicted interaction score between the compound for learning and the protein for learning output through the third neural network 33 from the ground truth interaction score.

Up to now, the structure of a deep-learning model and a method for training the deep-learning model according to a first embodiment of the present disclosure have been described with reference to FIG. 4. As described above, by independently constructing a neural network that extracts feature data from compound data and protein data, the performance of a deep-learning model may be improved.

In what follows, the structure of a deep-learning model and a method for training the deep-learning model according to a second embodiment of the present disclosure will be described with reference to FIGS. 5 and 6. In addition, in what follows, for the sake of clarity of the present disclosure, descriptions overlapping with the preceding embodiments will be omitted.

Figure 5:
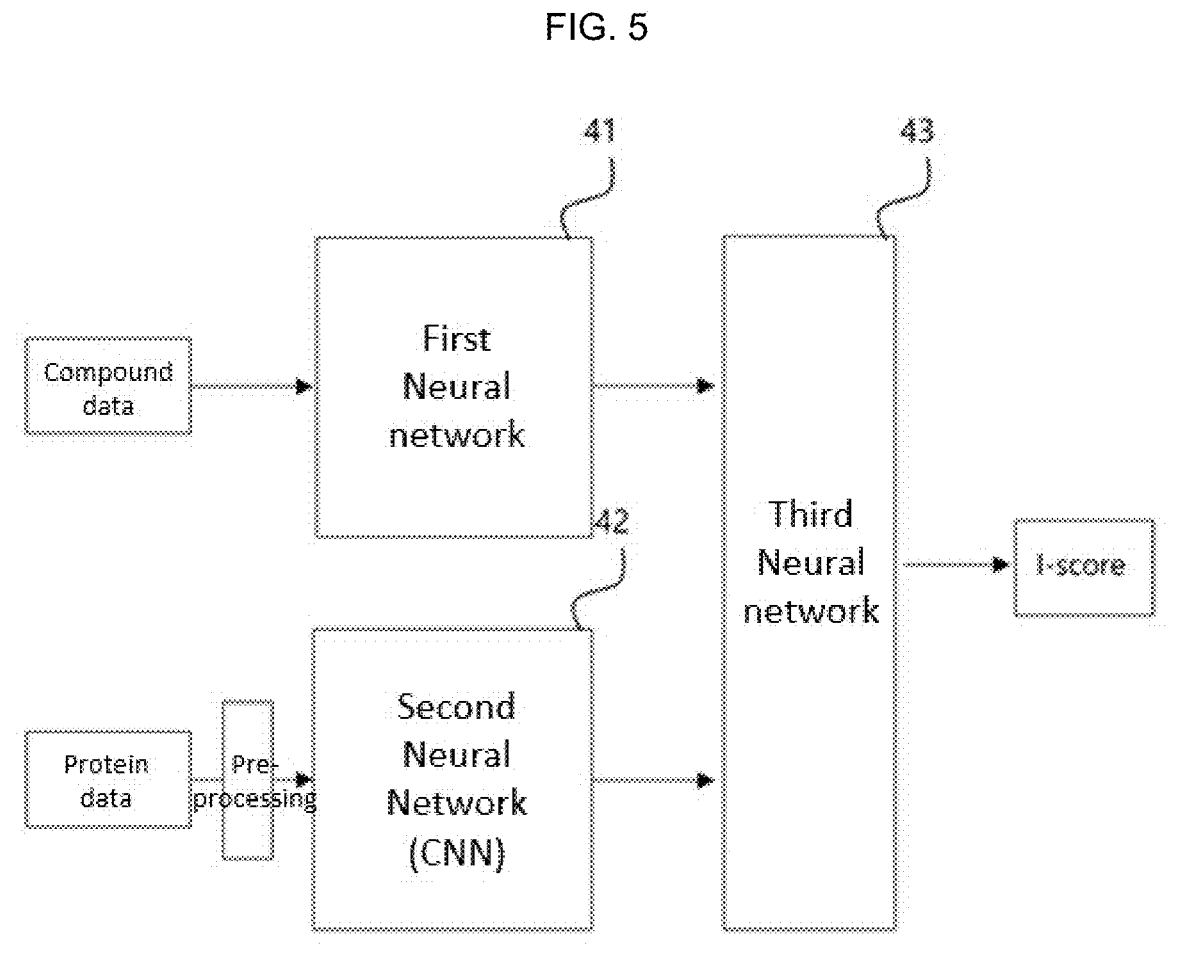

FIG. 5 illustrates the structure of a deep-learning model according to a second embodiment of the present disclosure.

As shown in FIG. 5, in the present embodiment, a second neural network 42 receiving protein data may be implemented based on a CNN. To be precise, at least a portion of the second neural network 42 receiving amino acid sequence data of the protein may be configured to include a CNN. Also, the amino acid sequence data may be converted into a two-dimensional image suitable for the CNN through a pre-processing process, and the converted two-dimensional (2-D) image may be input to the second neural network 42. However, specific pre-processing methods may vary depending on the embodiment.

In some embodiments, a plurality of n-gram sequences may be extracted from the amino acid sequence of the protein. In addition, a 2-D image may be generated by mapping a plurality of n-gram sequences onto a 2-D plane formed by two axes corresponding to amino acid types or amino acid sequences. At this time, the pixel values of the image may be set based on the number of n-gram sequences appearing in the amino acid sequence. To further facilitate understanding, additional descriptions will be given with reference to the example of FIG. 6.

Figure 6:
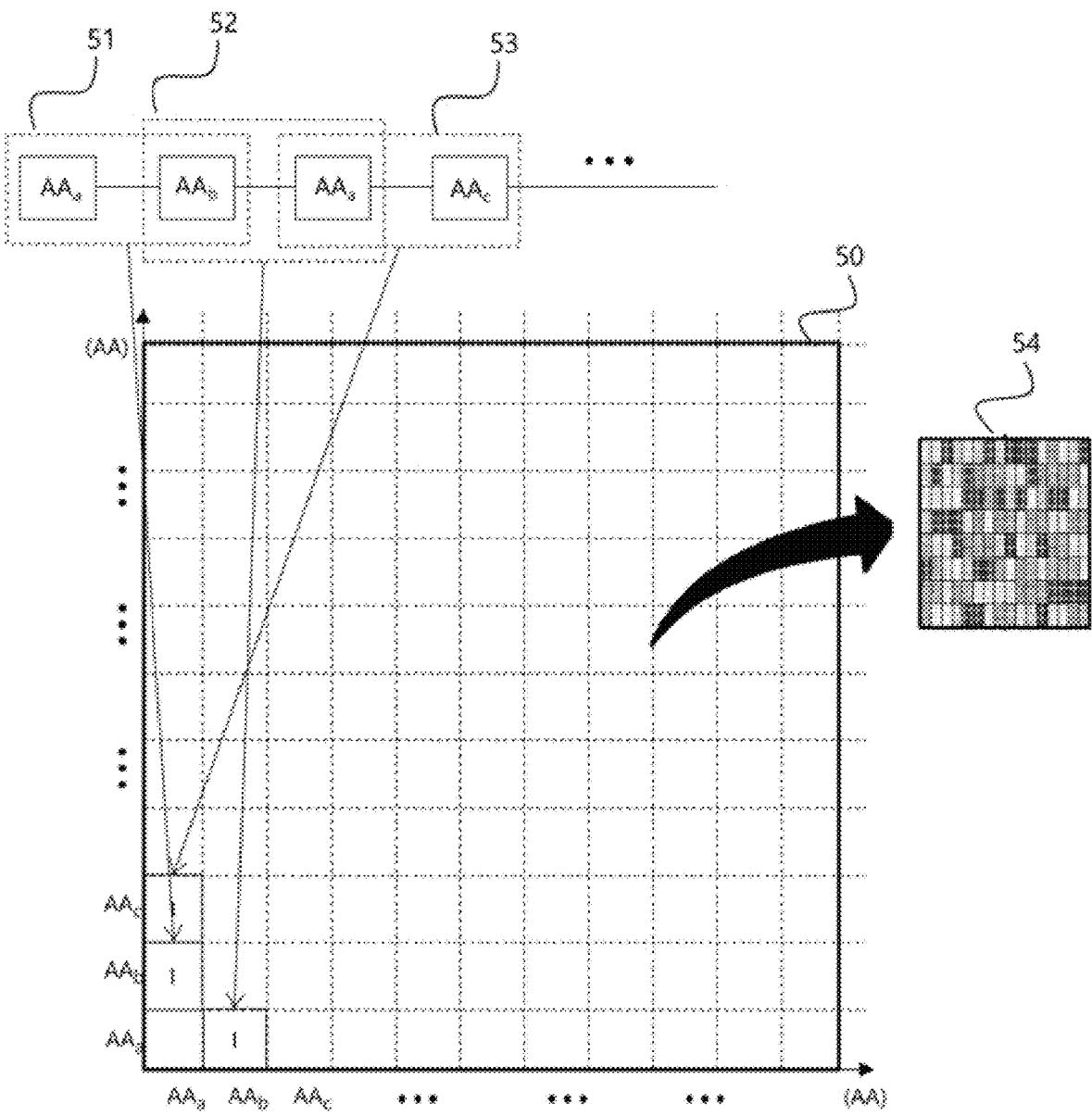

FIG. 6 shows an example of a process in which a bigram sequence extracted from an amino acid sequence (i.e., 51 to 53 if n is 2) is mapped onto a 2-D plane 50. For reference, in the following figures, "AA" refers to an amino acid, and an alphabetic subscript (a, b, c, and the like) that is not a numeric subscript refers to the type of amino acid.

As illustrated in FIG. 6, suppose that a plurality of bigram sequences 51-53 have been extracted from the amino acid sequences of a protein. In this case, a first bigram sequence 51 ("$AA_a$-$AA_b$") may be mapped to the coordinates (a, b) on the 2-D plane 50. As mapping is progressed, the pixel value at the coordinates (a, b) may be increased by a certain value (e.g., 1). In the same manner, a second bigram sequence 52 ("$AA_b$-$AA_a$") and a third bigram sequence 53 ("$AA_a$-$AA_c$") and the like may be mapped on the 2-D plane 50, and a 2-D image 54 may eventually be generated as the mapping process is repeated.

The first to third neural networks 41-43 may be trained by backpropagating errors based on the difference of a predicted interaction score between the compound for learning and the protein for learning output through the third neural network 43 from the ground truth interaction score. In addition, based on the learning, the second neural network 42 may be trained to extract local sequence patterns (features) that affect the interaction with a compound from a 2-D input image.

Meanwhile, FIG. 6 shows an example in which n is 2; however, the example is intended only to provide the convenience of understanding, and n may be 3 or more. If n is 3 or more, the X-axis and/or Y-axis may be designed to correspond to a predefined amino acid sequence (e.g., $AA_a$-$AA_a$, $AA_a$-$AA_b$, or $AA_b$-$AA_a$). Alternatively, mapping of n-gram sequences may be made by further utilizing a channel axis of the 2-D image.

Up to now, the structure of a deep-learning model and a method for training the deep-learning model according to the second embodiment of the present disclosure have been described with reference to FIGS. 5 and 6. As described above, an amino acid sequence of a protein may be converted to a 2-D image using the n-gram technique, and local sequence patterns (features) that affect the interaction with a compound may be extracted from a 2-D image through a CNN. Accordingly, the performance of the deep-learning model may be improved.

In what follows, the structure of a deep-learning model and a method for training the deep-learning model according to a third embodiment of the present disclosure will be described.

In the present embodiment, a deep-learning model may be implemented based on a CNN. In addition, compound data and protein data may be converted into a 2-D image suitable for the CNN through pre-processing, and the converted 2-D image may be input to the deep-learning model.

Specifically, a pair of a specific compound and a specific protein may be mapped on a 2-D plane formed by a first axis corresponding to the functional group of the compound and a second axis corresponding to the amino acid residue of the protein to produce a 2-D image. At this time, pixel values of the image may be set based on the degree of binding of the corresponding functional group and the amino acid residue. To provide further convenience of understanding, additional descriptions will be given with reference to the example shown in FIG. 7.

Figure 7:
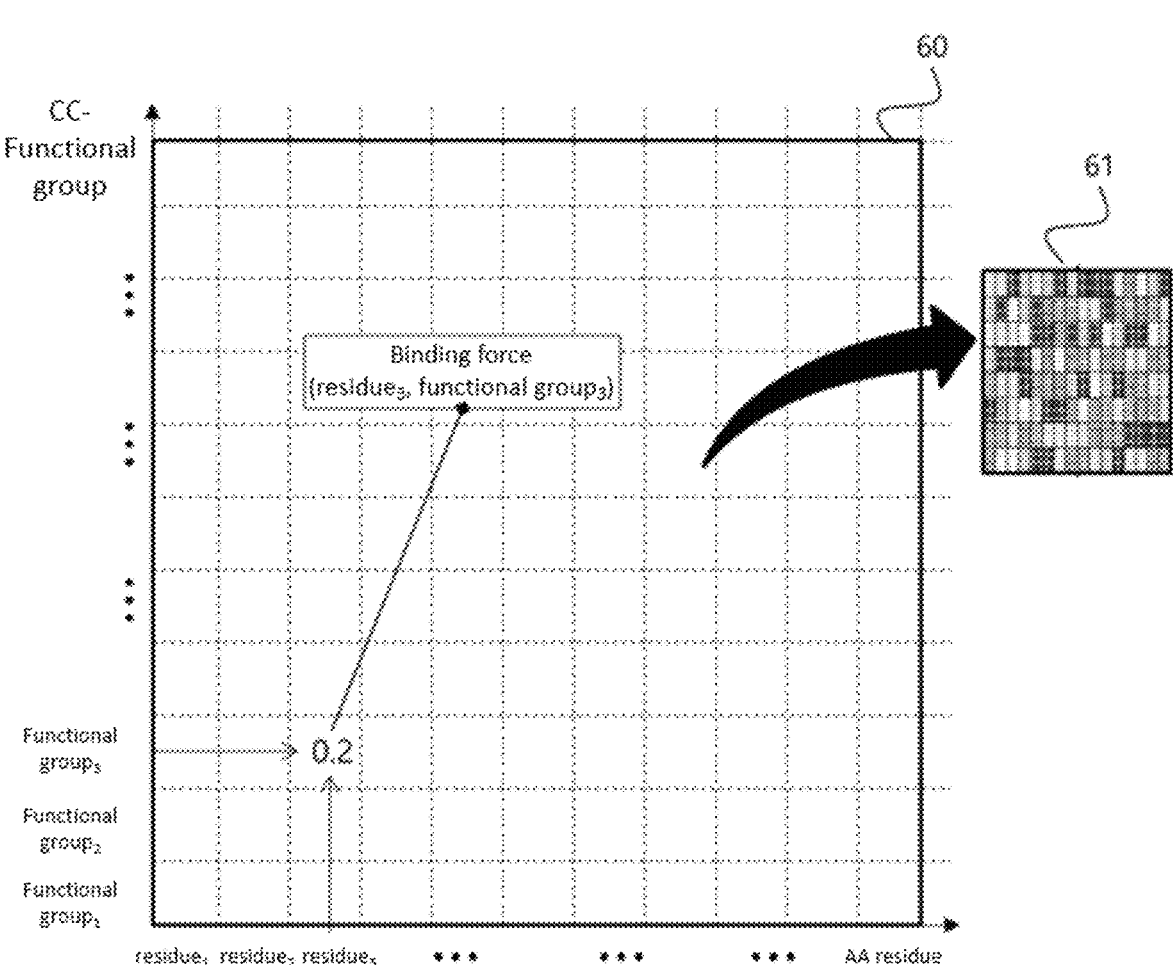
FIG. 7 illustrates a structure of a deep-learning model and a method for training the deep-learning model according to a third embodiment of the present disclosure.

FIG. 7 illustrates a process of mapping a pair of a protein and a compound onto the 2-D plane 60 using information on a residue and a functional group. In the following figures, "CC" refers to Chemical Compound.

As illustrated in FIG. 7, suppose that a compound includes a functional $group_3$ and a protein includes an amino acid $residue_3$. Then, a value indicating the degree of binding of the functional $group_3$ and the amino acid $residue_3$ may be assigned to the (functional $group_3$, amino acid $residue_3$) coordinates as a pixel value. As the process is repeated, a 2-D image 61 may be generated.

The deep-learning model according to the present embodiment may be trained by backpropagating errors based on the difference between the predicted interaction score acquired by inputting a 2-D image (e.g., 61) and the ground truth interaction score. In addition, based on the learning, the CNN of the deep-learning model may be trained to extract the binding pattern of amino acid residues and compound functional groups from a 2-D image.

Up to now, the structure of a deep-learning model and a method for training the deep-learning model according to the third embodiment of the present disclosure have been described with reference to FIG. 7. As described above, pairs of proteins and compounds may be converted into a 2-D image by considering the amino acid residues and compound functional groups, and residue-functional group binding patterns (features) that affect the interaction between a protein and a compound may be extracted from the 2-D image. Accordingly, the performance of the deep-learning model may be improved.

In what follows, the structure of a deep-learning model and a method for training the deep-learning model according to a fourth embodiment of the present disclosure will be described.

In the present embodiment, a deep-learning model may be configured to include an RNN-based embedding layer and a neural network. To be precise, a neural network receiving amino acid sequence data of a protein (e.g., the second neural network 32 of FIG. 4) may be configured to include an embedding layer and a neural network layer, the embedding layer may be trained to output an embedding vector, and the neural network layer may be trained to extract feature data of the corresponding protein from the embedding vector through neural network operations. In addition, the amino acid sequence data may be converted into an input data (vector) of the embedding layer through pre-processing. However, specific pre-processing techniques may vary depending on the embodiments.

In some embodiments, a plurality of n-gram sequences may be extracted from the amino acid sequence of the protein. In addition, a plurality of n-gram sequences may be converted to a vector form and input into the embedding layer. To provide further convenience of understanding, additional descriptions will be given with reference to the example shown in FIG. 8.

Figure 8:
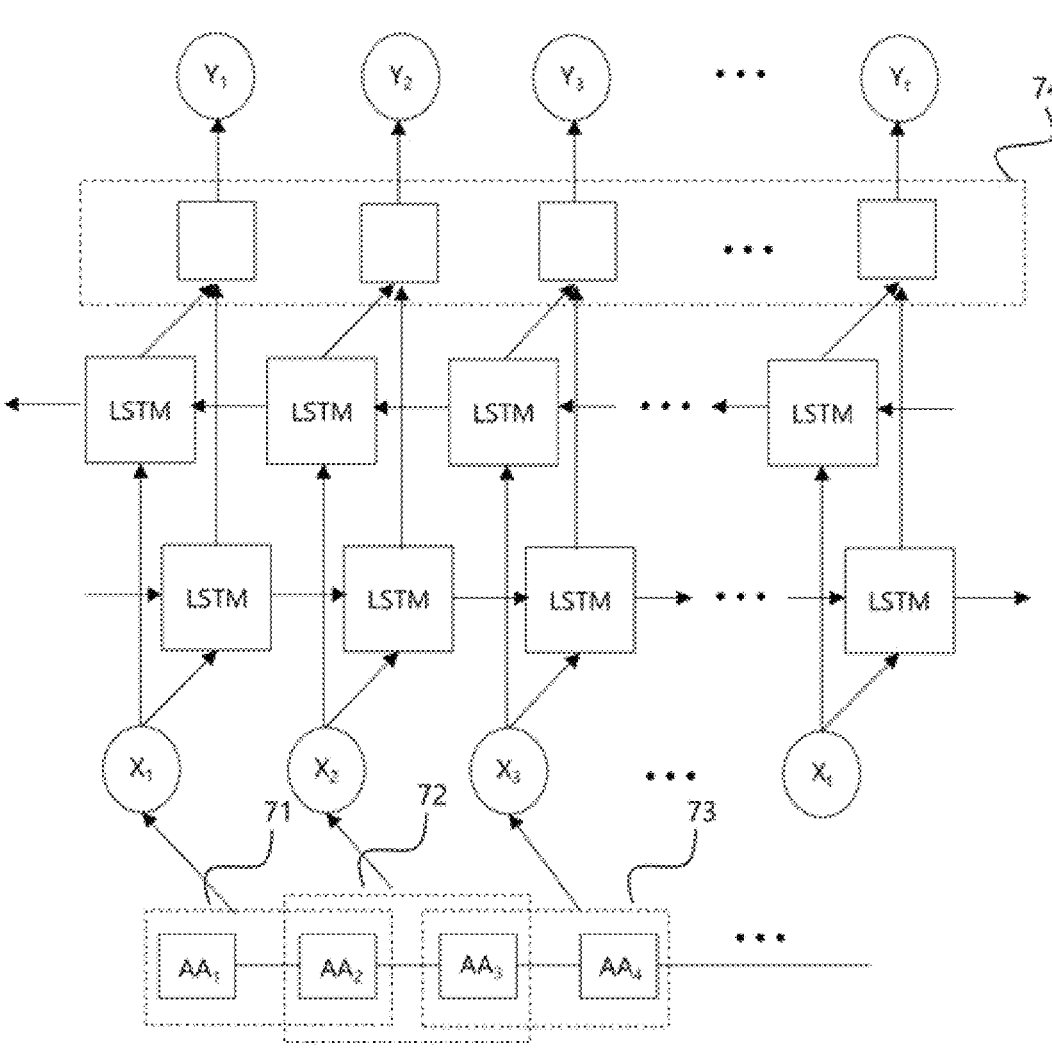
FIG. 8 illustrates a structure of a deep-learning model and a method for training the deep-learning model according to a fourth embodiment of the present disclosure.

FIG. 8 illustrates a process in which bigram sequences 71-73 extracted from the amino acid sequence of a protein are converted into embedding vectors ($Y_1$ to $Y_t$) through Bi-Long Short Term Memory (LSTM) based embedding layers.

As illustrated in FIG. 8, suppose that a plurality of bigram sequences 71-73 have been extracted from the amino acid sequences of a protein. In this case, each bigram sequence 71-73 may be converted into a bigram vector and input into an embedding layer. Any technique may be employed for converting a bigram sequence to a vector, where a known technique such as Back of Words (BoW) may be used.

The embedding layer may be trained to output embedding vectors ($Y_1$ to $Y_t$) by performing a neural network operation on the input bigram vectors ($X_1$ to $X_t$). In some embodiments, a neural network layer 74 may be disposed within the embedding layer. In this case, the neural network layer 74 may be trained to synthesize the output values of the RNN layer (e.g., a layer consisting of LSTM units) to generate embedding vectors ($Y_1$ to $Y_t$).

Up to now, the structure of a deep-learning model and a method for training the deep-learning model according to the fourth embodiment of the present disclosure have been described with reference to FIG. 7. As described above, amino acid sequences may be converted into embedding vectors through an RNN-based embedding layer. At this time, since the RNN may generate an embedding vector conveying features reflecting a sequential arrangement of amino acids, the performance of the deep-learning model may be improved.

In what follows, the structure of a deep-learning model and a method for training the deep-learning model according to a fifth embodiment of the present disclosure will be described.

The present embodiment relates to a method for constructing a deep-learning model to predict the interaction more accurately between a given compound and protein in an in vivo environment. Before setting out describing the present embodiment, for the convenience of understanding, the background of the present embodiment will be described briefly with reference to FIG. 9.

Figure 9:
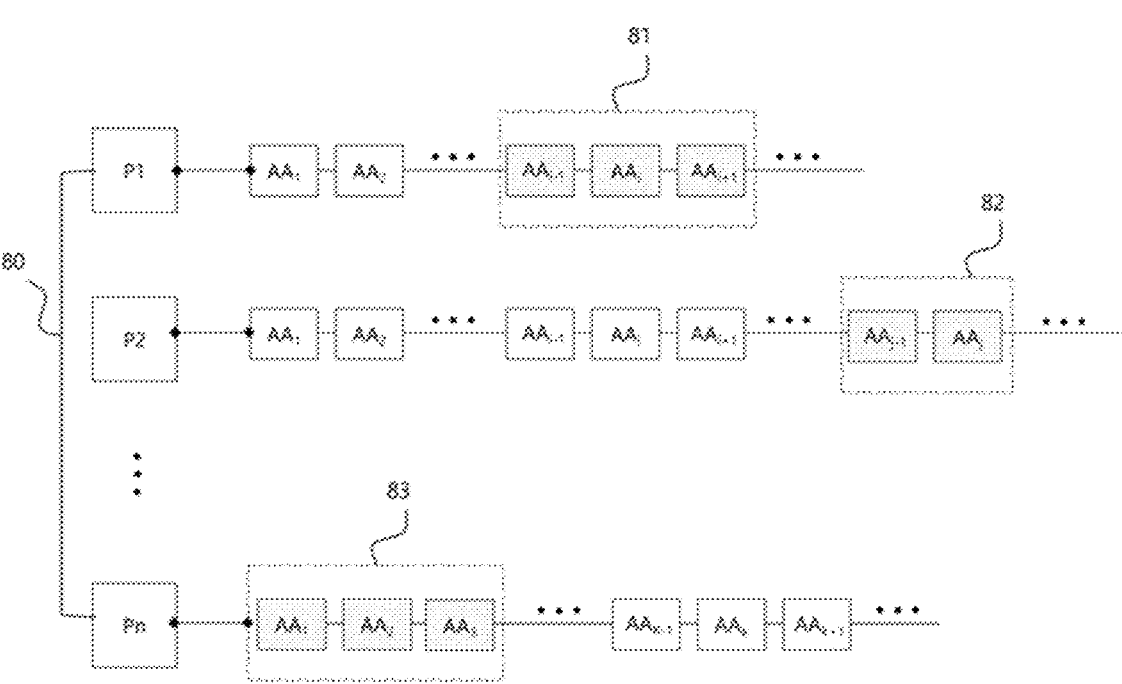
FIGS. 9, 10 and 11 illustrate a method for training a deep-learning model according to a fifth embodiment of the present disclosure.

As mentioned above, training data such as amino acid sequence data and interaction scores of a protein for learning may be acquired from a public DB. For example, amino acid sequence data 80 for learning of proteins P1 to $P_n$ as illustrated in FIG. 9 may be acquired from a public DB. Here, the amino acid sequences for learning of proteins (e.g., P1) may comprise sequences 81-83 associated with a specific protein domain, wherein the specific protein domain may include, for example, a transmembrane domain, an extracellular domain, or a subcellular organelles membrane domain and may include various other domains.

Meanwhile, it is well-known that a protein having amino acid sequences associated with a particular protein domain is more likely to be in the corresponding protein domain in vivo. For example, it is well-known that a protein (e.g., membrane protein including a plasma membrane receptor) having sequences associated with a transmembrane domain is likely to be in the transmembrane site and function as a transmembrane protein. Therefore, depending on which domain the amino acid sequence of a protein is associated with, the degree of interaction between a compound and the protein in vivo may vary greatly. For example, since a protein with amino acid sequences associated with the transmembrane domain is in the transmembrane site (domain) in vivo, the possibility of the protein interacting with the compound may be significantly decreased. Alternatively, a protein having amino acid sequences associated with an extracellular domain may interact better with a compound as the protein is in the extracellular site (domain) in vivo.

However, since the interaction scores between a compound and a protein provided by public DBs (or sites) are mostly measured in a laboratory environment (in vitro) rather than in vivo environment, the interaction scores do not reflect the degree of interaction that may vary depending on the protein domains. Therefore, it is difficult for a deep-learning model constructed based on the original data of the corresponding DB to accurately predict the degree of interaction between a compound and a protein in vivo. For example, a compound and a protein predicted to interact well based on a deep-learning model may not interact as expected in vivo, in which case the utility of the deep-learning model may be significantly reduced, and the development process of new drugs may be delayed, for example.

In what follows, the structure of a deep-learning model and a method for training the deep-learning model according to a fifth embodiment of the present disclosure to solve the problem above will be described.

In the present embodiment, pre-processing of training data and/or learning the training data may be performed in a manner different from the preceding embodiments to reflect the effect of a protein domain on the degree of interaction with a compound in a deep-learning model. However, specific methods for pre-processing and learning may vary.

In a first example, the interaction score of training data may be adjusted by considering the effect of a protein domain on the degree of interaction. Specifically, the interaction score of a first protein for learning, which includes an amino acid sequence (in what follows, abbreviated as a "negative amino acid sequence") associated with a protein domain (in what follows, abbreviated as a "negative domain" e.g., a transmembrane domain or a subcellular organelles membrane domain) having a negative effect, may be lowered. In contrast, the interaction score of training data may be adjusted. Specifically, the interaction score of a second protein for learning, which includes an amino acid sequence (in what follows, abbreviated as a "positive amino acid sequence") associated with a protein domain (in what follows, abbreviated as a "positive domain"; e.g., an extracellular domain) having a positive effect, may be increased. At this time, the increment may vary depending on the extent to which a protein domain affects the interaction with a compound, the number of associated amino acid sequences contained in the protein, and so on. In addition, a deep-learning model may be trained using training data with adjusted interaction scores. In this case, since the deep-learning model is trained through interaction scores adjusted by considering the in vivo environment, the deep-learning model may more accurately predict the interaction in the in vivo environment. Accordingly, the utility of the deep-learning model may be improved.

Figure 10:
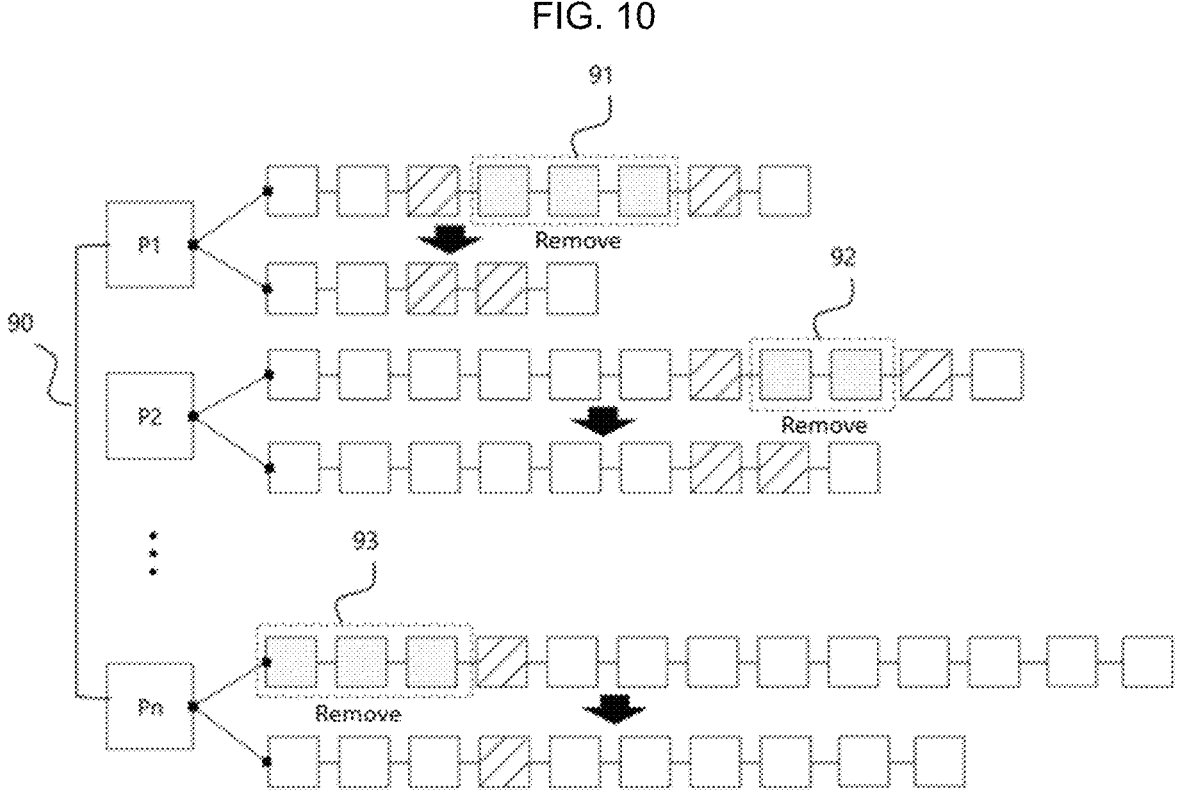

In a second example, pre-processing may be performed to remove a positive amino acid sequence and/or a negative amino acid sequence from the amino acid sequence data of the protein for learning. As shown in FIG. 10, the amino acid sequence data 90 of a protein (P1 to $P_n$) for learning may be newly constructed (generated) through pre-processing that removes negative amino acid sequences 91-93 from the amino acid sequences from the amino acid sequences of a protein for learning (P1 to $P_n$). Also, a deep-learning model may be trained using training data including amino acid sequence data 90, compound data for learning, and interaction scores. In this case, since a deep-learning model may be prevented from being trained by amino acid sequences that negatively affect the interaction with a compound having high interaction scores, the performance and utility of the deep-learning model may be improved.

Figure 11:
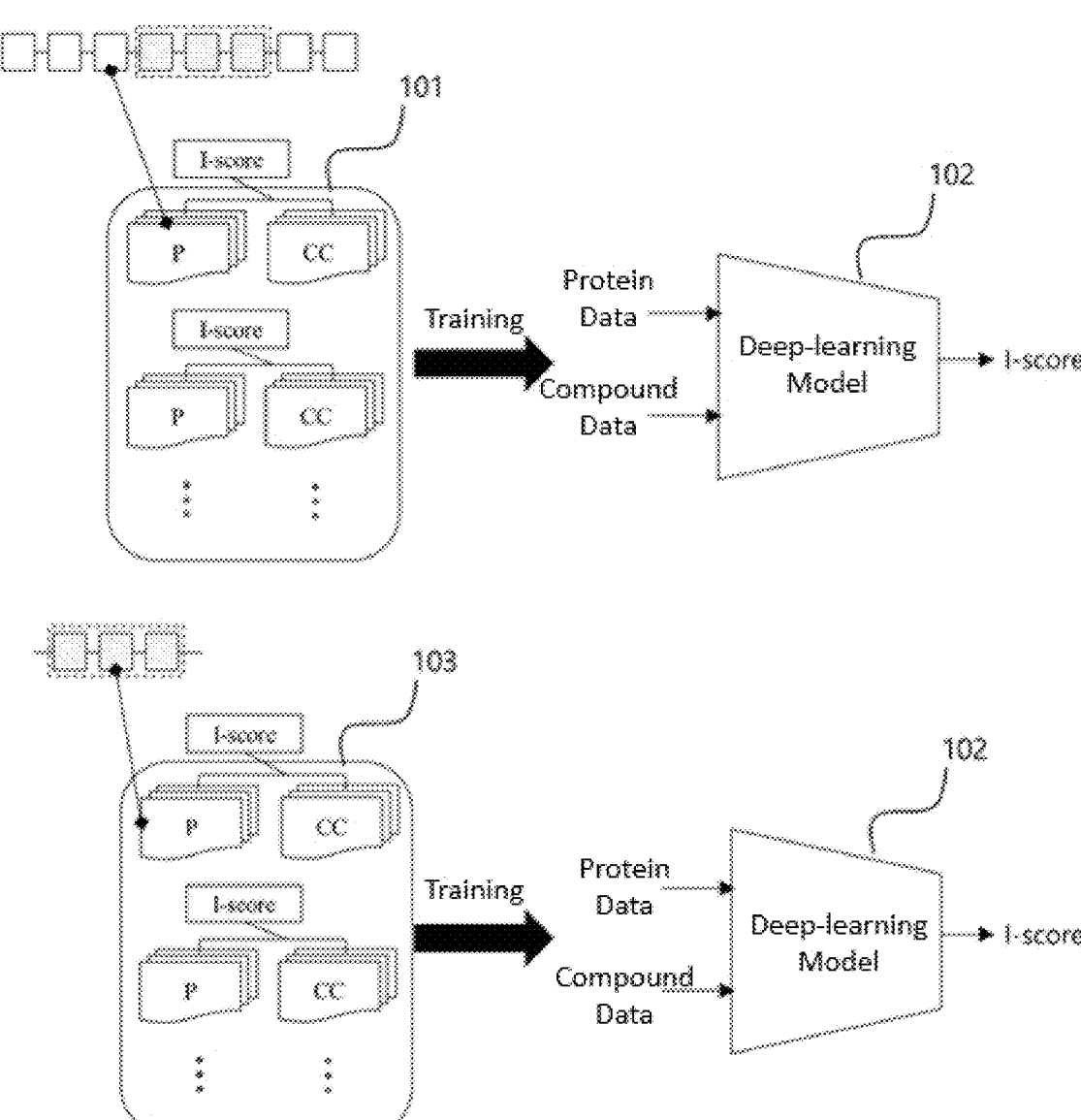

In a third example, as shown in FIG. 11, first training may be performed on the deep-learning model 102 using the original training data 101 for which the removal pre-processing has not been performed. In addition, second training may be performed on the deep-learning model 102 using negative amino acid sequences and/or positive amino acid sequences acquired (or known) through the removal pre-processing. Specifically, the second training may be performed using training data 103 consisting of negative amino acid sequences and/or positive amino acid sequences, compound data, and interaction scores. At this time, the interaction score of the training data 103 may be determined based on the effect on the interaction exerted by the positive domain or negative domain. For example, the interaction score of a negative amino acid sequence associated with a transmembrane domain may be set to a very low value (e.g., a value in the bottom 10%, such as 0). In the present disclosure, the second training may be performed after or before the first training or performed simultaneously with the first training. According to the present example, the extent to which a negative amino acid sequence and/or a positive amino acid sequence affects the interaction may be reflected in the deep-learning model through a separate training process. As a result, since the deep-learning model may make predictions by considering the in vivo environment, the performance and utility of the deep-learning model may be improved.

Meanwhile, in a fourth example, post-processing may be performed to adjust interaction scores during the prediction process of the deep-learning model. Specifically, after predicting the interaction score between a given protein and compound through a trained deep-learning model, the prediction device 10 may adjust the predicted interaction score according to the extent to which the given protein comprises a positive amino acid sequence and/or a negative amino acid sequence. At this time, the amount of adjustment may vary depending on the degree to which a protein domain associated with the given protein affects the interaction with the compound, the number of associated amino acid sequences contained in the protein, and the like.

In a fifth example, a deep-learning model may be trained and utilized based on various combinations of the preceding examples.

So far, methods for training a deep-learning model according to the fifth embodiment of the present disclosure have been described with reference to FIGS. 9 to 11. According to the methods, a deep-learning model may be trained by considering the relationship between a protein domain and interaction. As a result, since a deep-learning model may accurately predict interactions in the in vivo environment, the utility of the deep-learning model may be greatly improved.

In what follows, a method for training a deep-learning model according to a sixth embodiment of the present disclosure will be described.

The present embodiment relates to a method for further improving the performance of a deep-learning model using analysis results of training data, and more specifically, to a method for training a deep-learning model (e.g., weighted training or additional training) using a common amino acid sequence of proteins showing a strong degree of interaction with a specific compound or a common amino acid sequence of proteins with a weak degree of interaction. In what follows, the present embodiment will be described with reference to FIGS. 12 and 13.

Figure 12:
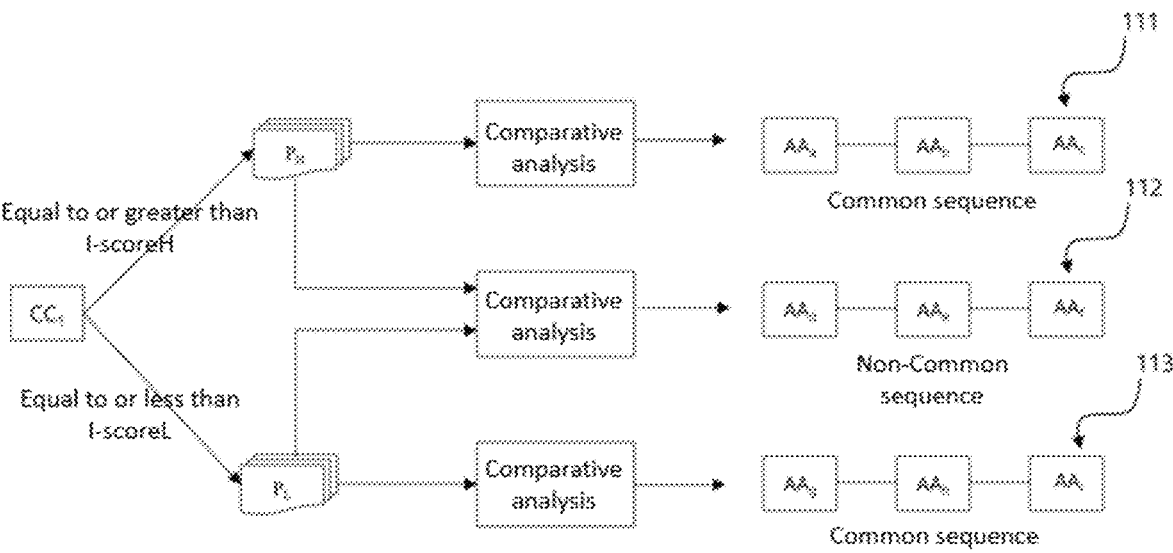
FIGS. 12 and 13 illustrate a method for training a deep-learning model according to a sixth embodiment of the present disclosure.
Figure 13:
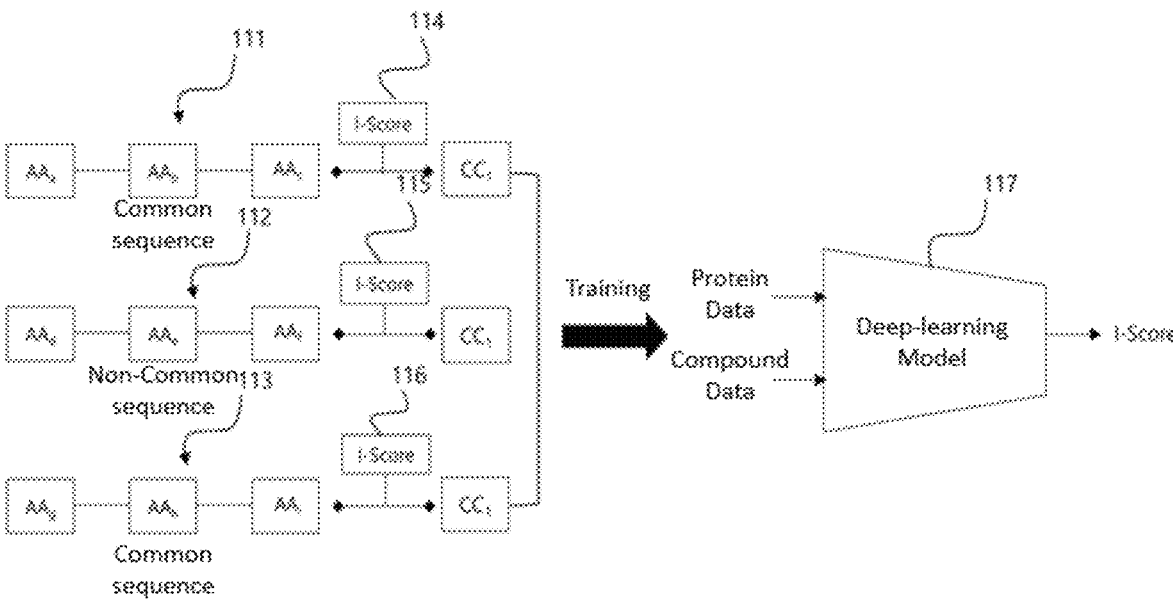

FIG. 12 illustrates a process of analyzing training data and extracting primary amino acid sequences, and FIG. 13 illustrates a process of training a deep-learning model 117 using the extracted major amino acid sequences.

As shown in FIG. 12, a first plurality of proteins for learning $P_H$ whose interaction score I-score with a compound for learning $CC_1$ is equal to or greater than a first threshold (e.g., I-scoreH) and a second plurality of proteins $P_L$ whose interaction score is equal to or less than a second threshold (e.g., I-scoreL) may be selected from training data. Also, common sequences 111, 113 and a non-common sequence 112 may be extracted by comparatively analyzing amino acid sequences of a plurality of selected proteins $P_H$, $P_L$ for learning.

For example, a first common sequence 111 may be extracted by comparatively analyzing the amino acid sequences of a first plurality of proteins $P_H$ for learning. Here, the first common sequence 111 may include an amino acid sequence commonly found in the first plurality of proteins $P_H$ for learning or an amino acid sequence similar to the commonly found amino acid sequence. Any method may be employed for extracting the first common sequence 111.

As another example, a second common sequence 113 may be extracted by comparatively analyzing the amino acid sequences of a second plurality of proteins $P_L$ for learning. Here, the second common sequence 113 may include an amino acid sequence commonly found in the second plurality of proteins $P_L$ for learning or an amino acid sequence similar to the commonly found amino acid sequence. Any method may be employed for extracting the second common sequence 113.

As yet another example, a non-common sequence 112 may be extracted by comparatively analyzing amino acid sequences of the first plurality of proteins $P_H$ for learning and the second plurality of proteins $P_L$ for learning. In other words, a non-common sequence 112 may be extracted based on the difference between amino acid sequences of the first plurality of proteins $P_H$ for learning and the second plurality of proteins $P_L$ for learning. Any method may be employed for extracting the non-common sequence 112.

Meanwhile, in some embodiments, a process of selecting amino acid sequences to be used for actual training from the amino acid sequences extracted as described above (e.g., 111 to 113) may be further performed. For example, from the amino acid sequences (e.g., 111 to 113), amino acid sequences whose sequence length is equal to or longer than a threshold may be selected as a learning target. This is because the shorter the sequence length, the less likely it is that the corresponding sequence affects the interaction. In another example, a deep-learning model trained for the selection process may be used. Specifically, an amino acid sequence to be learned may be selected based on the predicted interaction score output through the deep-learning model. For example, in the case of the first common sequence 111, the sequence may be selected as a learning target when the predicted interaction score is equal to or greater than the first threshold (e.g., I-scoreH). Also, in the case of the second common sequence 113, the sequence may be selected as a learning target when the predicted interaction score is equal to or less than the second threshold (e.g., I-scoreL). Also, in the case of the non-co-operative sequence 112, the sequence may be selected as a learning target when the predicted interaction score is equal to or greater than the first threshold (e.g., I-scoreH) or equal to or less than the second threshold (e.g., I-scoreL).

In what follows, a process of training (e.g., additional training) a deep-learning model 117 will be described with reference to FIG. 13.

As shown in the figure, a deep-learning model 117 may be trained using compound data $CC_1$ for learning and training data made up of a first common sequence 111 and a first interaction score 114. At this time, the first interaction score 114 may be set to a value higher than the first threshold (e.g., I-scoreH) or an average interaction score of the first plurality of proteins $P_H$. By doing so, a positive effect of the first common sequence 111 on the interaction with the compound $CC_1$ may be strongly reflected in the deep-learning model 117. In some examples, the first interaction score 114 may be determined based on a predicted interaction score between the compound $CC_1$ for learning and the first common sequence 111 output through the deep-learning model 117. For example, the first interaction score 114 may be determined by a value higher than the predicted interaction score.

Alternatively, the deep-learning model 117 may be trained using data of the compound for learning $CC_1$ and the training data made up of the second common sequence 113 and the second interaction score 116. At this time, the second interaction score 116 may be set to a value lower than the first threshold (e.g., I-scoreL) or an average interaction score of the second plurality of proteins $P_L$. By doing so, a negative effect of the second common sequence 113 on the interaction with the compound $CC_1$ may be strongly reflected in the deep-learning model 117. In some examples, the second interaction score 116 may be determined based on a predicted interaction score between the compound $CC_1$ for learning and the second common sequence 113 output through the deep-learning model 117. For example, the second interaction score 116 may be determined by a value lower than the predicted interaction score.

Alternatively, the deep-learning model 117 may be trained using data of the compound for learning $CC_1$ and the training data made up of the non-common sequence 112 and a third interaction score 115. At this time, the third interaction score 115 may be determined based on a predicted interaction score of the deep-learning model 117. For example, when the predicted interaction score between the compound for learning $CC_1$ and the non-common sequence 113 output through the deep-learning model 117 is similar to the third threshold (e.g., I-scoreH), the third interaction score 115 may be determined by a value higher than the predicted interaction score. On the other hand, when the predicted interaction score is similar to the second threshold (e.g., I-scoreL), the third interaction score 115 may be determined by a value lower than the predicted interaction score.

Meanwhile, in some embodiments, weighted training may be performed on the deep-learning model 117 for each sample that constitutes the training data based on sample weights. At this time, a sample weight may be determined in various ways. For example, the weight of a first sample to which the first common sequence 111 belongs may be determined based on the length and/or frequency of appearance of the first common sequence 111. As a more specific example, the longer the length of the first common sequence 111 or the higher the frequency with which the first common sequence 111 appears in the first plurality of proteins $P_H$, the higher weight may be given to the first sample. Also, the weight of a second sample to which the second common sequence 111 belongs may be assigned in the same manner as the first sample. Also, the weight of a third sample to which the non-common sequence 112 belongs may be determined based on a predicted interaction score of the deep-learning model 117. For example, a higher weight may be assigned to the third sample as the predicted interaction score becomes higher than the first threshold (e.g., I-scoreH) or lower than the second threshold (e.g., I-scoreL).

In the preceding embodiment, a specific method for weighted training may be performed in various ways, for example, by increasing the number of training trials (e.g., the number of training trials is increased as the sample weight becomes higher) or by amplifying the prediction error (e.g., as a sample weight becomes higher, the prediction error of the corresponding sample is amplified), and any method may be employed for performing the weighted training.

So far, a method for training a deep-learning model according to the sixth embodiment of the present disclosure has been described with reference to FIGS. 12 and 13. As described above, a deep-learning model may be trained separately using major amino acid sequences (in other words, sequences expected to exert a large influence on the interaction) derived through comparative analysis of training data. Accordingly, the performance of the deep-learning model may be further improved.

Figure 14:
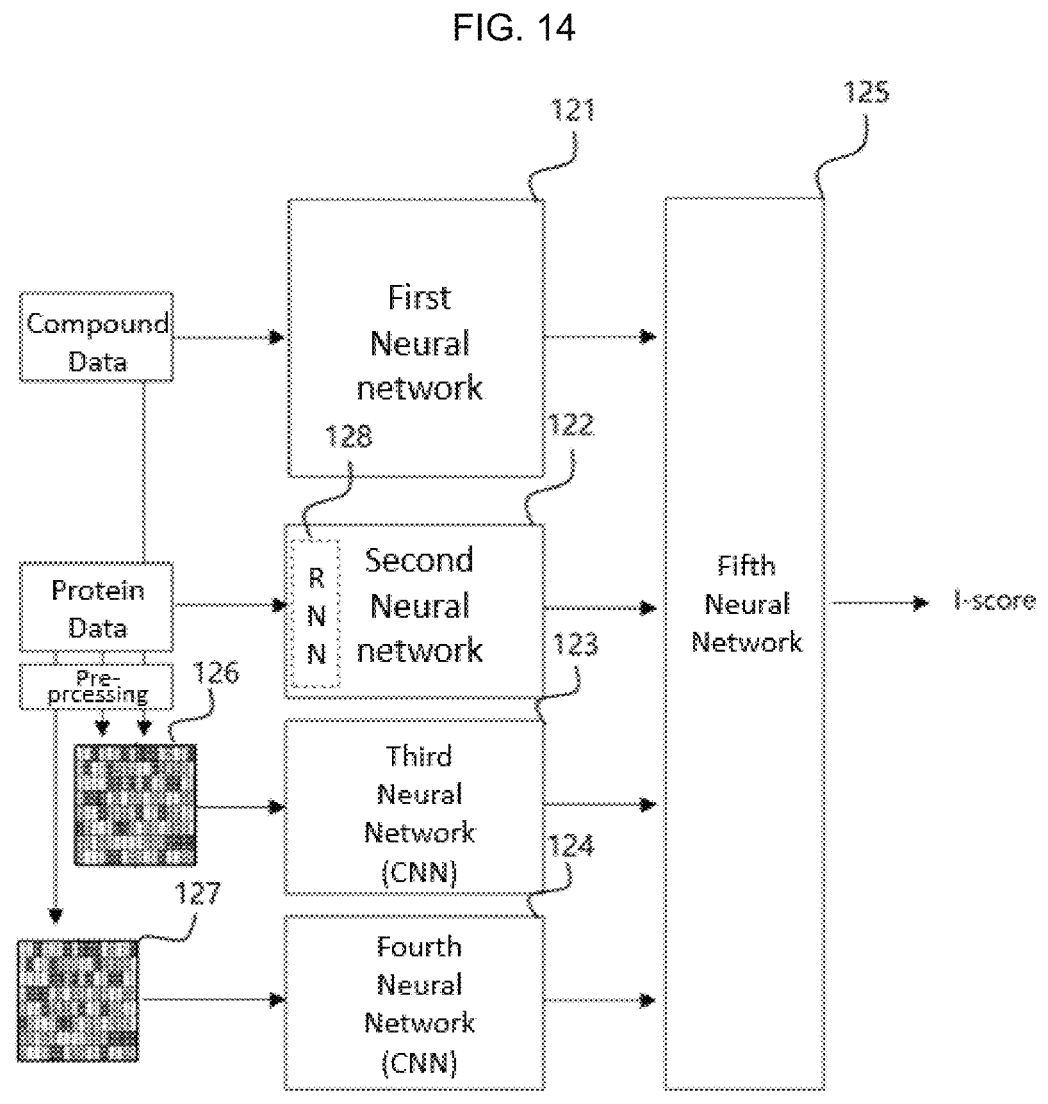

Meanwhile, the first to sixth embodiments described so far may be combined in various ways. For example, as shown in FIG. 14, a deep-learning model according to some embodiments may consist of the first to fifth neural networks 121-125, and the second neural network 122 may include an RNN-based embedding layer 128 (refer to the fourth embodiment). The third 123 and fourth neural networks 124 may be implemented based on the CNN, and each neural network 123, 124 may receive images 126, 127 generated according to the second and third embodiments as an input. Also, the fifth neural network 125 may synthesize feature data extracted from the first to fourth neural networks 121-124 to predict interaction scores.

In what follows, a computing device 130 capable of implementing the prediction device 10 according to some embodiments of the present disclosure will be described.

FIG. 15 illustrates a hardware structure of the computing device 130.

As shown in FIG. 15, the computing device 130 may comprise one or more processors 131, a bus 133, a communication interface 134, a memory 132 that loads a computer program performed by the processor 131, and a storage 135 that stores the computer programs 136. However, FIG. 15 shows only those constituting elements related to the embodiment of the present disclosure. Accordingly, it should be understood by those skilled in the art to which the present disclosure belongs that other general-purpose constituting elements may be further included in addition to the constituting elements shown in FIG. 15. In other words, the computing device 130 may further include various constituting elements in addition to the constituting elements shown in FIG. 15. Alternatively, the computing device 130 may be composed by excluding some of the constituting elements shown in FIG. 15.

The processor 131 may control the overall operation of each configuration of the computing device 130. The processor 131 may be configured by including at least one of a Central Processing Unit (CPU), a Micro-Processor Unit (MPU), a Micro-Controller Unit (MCU), a Graphics Processing Unit (GPU), or any arbitrary type of processor well known to the technical field of the present disclosure. Also, the processor 131 may perform operations on at least one application or program for executing the methods/operations according to embodiments of the present disclosure. The computing device 130 may be equipped with one or more processors.

Next, the memory 132 may store various data, instructions, and/or information. The memory 132 may load one or more computer programs 136 from the storage 135 to execute the methods/operations according to the embodiments of the present disclosure. The memory 132 may be implemented using a volatile memory such as RAM but is not limited thereto.

Next, the bus 133 may provide a communication function between the constituting elements of the computing device 130. The bus 133 may be implemented using various types of buses such as an address bus, a data bus, and a control bus.

Next, the communication interface 134 may support wired and wireless Internet communication of the computing device 130. In addition, the communication interface 134 may support various communication schemes in addition to Internet communication. To this end, the communication interface 134 may be configured to include a communication module well known in the technical field of the present disclosure.

Next, the storage 135 may store the one or more programs 136 non-temporarily. The storage 135 may be configured to include non-volatile memory such as a Read-Only Memory (ROM), an Erasable Programmable ROM (EPROM), an Electrically Erasable Programmable ROM (EEPROM), and a flash memory; a hard disk; a removable disk; or any type of computer-readable recording medium well known in the technical field to which the present disclosure belongs.

Next, the computer program 136, when loaded into the memory 132, may include one or more instructions that instruct the processor 131 to perform the methods/operations according to various embodiments of the present disclosure. In other words, by executing the one or more instructions, the processor 131 may perform the methods/operations according to various embodiments of the present disclosure.

For example, the computer program 136 may include instructions that instruct the processor to perform an operation of acquiring training data consisting of compound data for learning, protein data for learning, and interaction scores, an operation of constructing a deep-learning model using the acquired training data, and an operation of predicting the interaction between a given compound and protein through the constructed deep-learning model. In this case, the prediction device 10 according to some embodiments of the present disclosure may be implemented through the computing device 130.

The technical principles and spirit of the present disclosure, described so far with reference to FIGS. 1 to 15, may be implemented in computer-readable code on a computer-readable medium. The computer-readable recording medium may include, for example, a removable recording medium (CD, DVD, Blu-ray Disc, USB storage device, removable hard disk), or a stationary recording medium (ROM, RAM, or a built-in computer hard disk). The computer program recorded in a computer-readable recording medium may be transmitted to a different computing device through a network such as the Internet and installed in the different computing device, thereby being used in the different computing device.

In the above, just because all the constituting elements comprising an embodiment of the present disclosure are combined into one or operate in combination with each other does not mean that the technical principles and spirit of the present disclosure are necessarily limited to the embodiment. In other words, as long as being within the technical scope of the present disclosure, all the constituting elements may operate by being selectively integrated into one or more combinations.

Although the operations are shown in a particular order in the figure, it should not be understood that the operations have to be performed in that order or in the sequential order according to which the operations are shown or that a desired result may be achieved only when all the illustrated operations are executed. In certain situations, multitasking and parallel processing may be advantageous. Moreover, separation into various configurations in the embodiments described above should not be understood as being required necessarily, and the program components and systems described above may generally be integrated into a single software product or packaged into multiple software products.

So far, although the embodiments of the present disclosure have been described with reference to appended drawings, it should be understood by those skilled in the art to which the present disclosure belongs that the present disclosure may be embodied in other specific forms without changing the technical principles or essential characteristics of the present disclosure. Therefore, the embodiments described above should be regarded as being illustrative rather than restrictive in every aspect. The technical scope of the present disclosure should be determined by the appended claims given below, and it should be understood that all of the technical principles found within the range equivalent to the technical scope of the present disclosure should be interpreted to belong thereto.

What is claimed is:

1. A method for predicting interaction between a compound and a protein in a computing device, the method comprising:

acquiring training data composed of compound data for learning, protein data for learning, and interaction scores;

constructing a deep-learning model using the acquired training data, the deep-learning model including a first neural network receiving a 2-D image generated from the protein data for learning, a second neural network receiving the compound data for learning, and a third neural network receiving a computation result of the second neural network and predicting an interaction score;

predicting interaction between a given compound and protein, wherein the protein data for learning includes amino acid sequences of the protein for learning, and the constructing includes generating first training data by excluding amino acid sequences associated with a first protein domain having a negative influence on the interaction in vivo from the amino acid sequences of the protein for learning; and training the deep-learning model using the first training data, wherein training the deep-learning model includes extracting a plurality of n-gram sequences from amino acid sequences of the first training data, generating the 2-D image by mapping the plurality of n-gram sequences on a 2-D plane formed by two axes corresponding to an amino acid type and an amino acid sequence and setting pixel values of the 2-D image based on the number of n-gram sequences appearing in the amino acid sequences, and performing the training by entering the 2-D image into the first neural network, extracting local sequence patterns from the 2-D image that affect the interaction with a compound, and backpropagating errors based on the difference of the predicted interaction between the compound for learning and the protein for learning output through the third neural network from the interaction scores.

2. The method of claim 1, wherein the first protein domain includes a transmembrane domain.

3. The method of claim 1, wherein the constructing includes generating second training data consisting of the compound data for learning, amino acid sequence data associated with the first protein domain, and a first interaction score; and training the deep-learning model using the second training data, wherein the first interaction score is determined based on the extent to which the first protein domain negatively affects the interaction.

4. The method of claim 1, wherein the constructing includes generating second training data consisting of the compound data for learning, amino acid sequence data associated with a second protein domain, and a first interaction score; and training the deep-learning model using the second training data, wherein the first interaction score is determined based on the extent to which the second protein domain positively affects the interaction.

5. The method of claim 4, wherein the second protein domain includes an extracellular domain.

6. The method of claim 1, wherein the first neural network includes a Recurrent Neural Network (RNN) layer and a neural network layer, wherein the RNN layer receives an n-gram vector extracted from an amino acid sequence and outputs an embedding vector of the corresponding amino acid sequence, and the neural network layer receives the embedding vector and performing neural computations.

7. The method of claim 1, wherein the constructing includes:

selecting, from the acquired training data, a first plurality of proteins for learning whose interaction score with a specific compound for learning is equal to or greater than a threshold and a second plurality of proteins for learning whose interaction scores are equal to or less than the threshold;

extracting a first common sequence by comparing amino acid sequences of the first plurality of proteins for learning;

extracting a second common sequence by comparing amino acid sequences of the second plurality of proteins for learning;

training the deep-learning model using second training data consisting of the first common sequence, the specific compound data for learning, and a first interaction score; and training the deep-learning model using third training data consisting of the second common sequence, the specific compound data for learning, and a second interaction score, wherein the first interaction score is set to a value higher than an average interaction score of the first plurality of proteins for learning, and the second interaction score is set to a value lower than an average interaction score of the first plurality of proteins for learning.

8. The method of claim 7, wherein the extracting the first common sequence includes:

extracting candidate common sequences by comparing amino acid sequences of the first plurality of proteins for learning;

acquiring a predicted interaction score between the candidate common sequences and the specific compound data for learning through the deep-learning model; and selecting a sequence for which the predicted interaction score is equal to or greater than a threshold among the candidate common sequences.

9. The method of claim 7, wherein the training the deep-learning model using the second training data includes:

determining a sample weight based on a length of the first common sequence and a frequency of appearance of the first common sequence in the first plurality of proteins for learning; and training the deep-learning model based on the determined sample weight.

10. The method of claim 1, wherein the constructing includes:

selecting a first protein for learning whose interaction score with a specific compound for learning is equal to or greater than a threshold and a second protein for learning whose interaction score is equal to or less than the threshold by analyzing the acquired training data;

extracting a non-common sequence by comparing the amino acid sequence of the first protein for learning and the amino acid sequence of the second protein for learning;

acquiring a predicted interaction score between the non-common sequence and the specific compound for learning through the deep-learning model and determining an interaction score for learning based on the predicted interaction score; and training the deep-learning model using second training data consisting of the non-common sequence, the specific compound data for learning, and the determined interaction score.

11. An apparatus for predicting interaction between a compound and a protein, the apparatus comprising:

a memory storing one or more instructions; and a processor configured to perform, by executing the stored one or more instructions, an operation of acquiring training data consisting of compound data for learning, protein data for learning, and interaction scores, an operation of constructing a deep-learning model using the acquired training data, the deep-learning model including a first neural network receiving a 2-D image generated from the protein data for learning, a second neural network receiving the compound data for learning, and a third neural network receiving a computation result of the second neural network and predicting an interaction score, and an operation of predicting interaction between a given compound and protein through the constructed deep-learning model, wherein the protein data for learning includes amino acid sequences of the protein for learning, the constructing operation includes an operation of generating first training data by excluding amino acid sequences associated with a first protein domain having a negative influence on the interaction in vivo from the amino acid sequences of the protein for learning; and an operation of training the deep-learning model using the first training data, wherein training the deep-learning model includes extracting a plurality of n-gram sequences from amino acid sequences of the first training data, generating the 2-D image by mapping the plurality of n-gram sequences on a 2-D plane formed by two axes corresponding to an amino acid type and an amino acid sequence, and performing the training by entering the 2-D image into the first neural network, extracting local sequence patterns from the 2-D image that affect the interaction with a compound, and backpropagating errors based on the difference of the predicted interaction between the compound for learning and the protein for learning output through the third neural network from the interaction scores.

12. A computer program stored in a computer-readable recording medium, the computer program, being combined with a computing device, comprising:

acquiring training data consisting of compound data for learning, protein data for learning, and interaction scores;

constructing a deep-learning model using the acquired training data, the deep-learning model including a first neural network receiving a 2-D image generated from the protein data for learning, a second neural network receiving the compound data for learning, and a third neural network receiving a computation result of the second neural network and predicting an interaction score; and predicting interaction between a given compound and protein through the constructed deep-learning model, wherein the protein data for learning includes amino acid sequences of the protein for learning, the constructing includes generating first training data by excluding amino acid sequences associated with a first protein domain having a negative influence on the interaction in vivo from the amino acid sequences of the protein for learning; and training the deep-learning model using the first training data, wherein training the deep-learning model includes extracting a plurality of n-gram sequences from amino acid sequences of the first training data, generating the 2-D image by mapping the plurality of n-gram sequences on a 2-D plane formed by two axes corresponding to an amino acid type and an amino acid sequence, and performing the training by entering the 2-D image into the first neural network, extracting local sequence patterns from the 2-D image that affect the interaction with a compound, and backpropagating errors based on the difference of the predicted interaction between the compound for learning and the protein for learning output through the third neural network from the interaction scores.

* * * * *